United States Patent [19]
Wilk et al.

[11] Patent Number: 5,176,692
[45] Date of Patent: Jan. 5, 1993

[54] METHOD AND SURGICAL INSTRUMENT FOR REPAIRING HERNIA

[76] Inventors: Peter J. Wilk, 185 W. End Ave., New York, N.Y. 10023; James Z. Cinberg, 167 N. Ridgewood Rd., South Orange, N.J. 07079

[21] Appl. No.: 803,568

[22] Filed: Dec. 9, 1991

[51] Int. Cl.⁵ .............................................. A61M 29/00
[52] U.S. Cl. ................................ 606/151; 606/108; 606/191; 606/195; 606/213; 606/1; 604/96; 604/103; 604/104
[58] Field of Search .................... 604/96, 194, 195, 11, 604/97–104; 606/192–194, 195, 154, 108, 191

[56]       References Cited
U.S. PATENT DOCUMENTS

| | | | |
|---|---|---|---|
| 2,701,559 | 2/1955 | Cooper | 606/192 |
| 3,483,859 | 12/1969 | Pittman | 604/96 |
| 4,441,495 | 4/1984 | Hicswa | 604/103 |
| 4,638,803 | 1/1987 | Rand | 606/192 |
| 4,685,447 | 8/1987 | Iversen et al. | 604/96 |
| 4,693,243 | 9/1987 | Buras | 604/96 |
| 4,733,665 | 3/1988 | Palmaz | 604/96 |
| 4,790,313 | 12/1988 | Borrelly | 604/96 |
| 4,823,815 | 4/1989 | Watson et al. | 604/96 |
| 5,092,841 | 3/1992 | Spears | 604/96 |

FOREIGN PATENT DOCUMENTS

| | | | |
|---|---|---|---|
| 2659440 | 7/1977 | Fed. Rep. of Germany | 604/96 |
| 3837779 | 5/1989 | Fed. Rep. of Germany | 604/96 |
| 9001969 | 3/1990 | World Int. Prop. O. | 604/96 |

Primary Examiner—Stephen C. Pellegrino
Assistant Examiner—Glenn Dawson
Attorney, Agent, or Firm—R. Neil Sudol; Henry D. Coleman

[57] ABSTRACT

A surgical instrument for use in hernia repair comprises an elongate tube having a distal end and a proximal end and a balloon attached in a collapsed configuration to the tube at the distal end, the balloon being made of a material which is absorbable by the human body. A net which envelops the balloon is also attached to the tube at the distal end thereof. During a hernia repair operation, the tube is used to insert the balloon from the abdominal cavity of a patient through a hernial opening in an abdominal wall of the patient and into a hernial pocket in inguinal tissue. After the balloon has been so inserted, it is inflated, which expands the net, and the abdominal wall opening is subsequently sealed. A mesh of biologically inert polymeric material for inducing human tissue growth is attached to the abdominal wall over the opening therein. The peritoneal tissue is stapled closed over the sealed opening in the abdominal wall.

22 Claims, 4 Drawing Sheets

METHOD AND SURGICAL INSTRUMENT FOR REPAIRING HERNIA

BACKGROUND OF THE INVENTION

This invention relates to a method for repairing a hernia. More particularly, this invention relates to a laparoscopic method for repairing a hernia. This invention also relates to a surgical instrument for use in hernia repair operations.

A hernia results when a person's abdominal wall is torn to form an opening. A portion of the person's internal body organs, including a portion of the peritoneal lining, is then displaced through the opening and into the inguinal tissues. Pain is generated upon the pinching of the displaced internal body organ or organs by the opening in the abdominal wall.

Although some progress has been made in simplifying hernial repair operations, for example, through the use of laparoscopic means, there is yet opportunity for improvement.

OBJECTS OF THE INVENTION

An object of the present invention is to provide an improved method for use in hernia repair operations.

Another object of the present invention is to provide an associated instrument for repairing hernias.

Another, more particular, object of the present invention is to provide such a method and associated instrument which are useful in a laparoscopic procedure.

A further particular object of the present invention is to provide such an instrument which is easy to use.

Yet another particular object of the present invention is to provide such an instrument which is easy and inexpensive to manufacture.

SUMMARY OF THE INVENTION

A surgical instrument for use in hernia repair comprises, in accordance with the present invention, an elongate rod-like member having a distal end and a proximal end and a balloon attached in a collapsed configuration to the rod-like member at he distal end, the balloon being made of a material which is absorbable by the human body. The balloon is expandable from the collapsed configuration to an expanded configuration, a component being operatively connected to the balloon for expanding or inflating the balloon from the collapsed configuration to the expanded configuration.

In accordance with another feature of the present invention, the balloon is provided with an element for inducing human tissue growth upon insertion and inflation of the balloon in a hernial pocket of a patient and upon subsequent absorption of the balloon by internal tissues of the patient. The tissue growth inducing element includes, in a specific embodiment of the present invention, a net-like member attached in a collapsed configuration to the rod-like member at the distal end thereof. The net-like member envelops the balloon and is made of a biologically inert and flexible polymeric material. In an alternative or complementary specific embodiment of the invention, the tissue growth inducing element includes a mesh web attached to the balloon at a proximal end thereof. The net-like member and the mesh web are advantageously provided with a plurality of outwardly extending projections. These projections serve to fix the balloon and the tissue growth inducing element to the patient. This fixing accelerates the healing process.

Pursuant to another feature of the present invention, the rod-like member is hollow and thereby takes the form of a tube. Preferably, at least a portion of the tube proximate to the balloon and located proximally thereof is made of a deformable material. This feature of the invention enables the tube, which acts as an insertion and disposition member, to be crimped and severed upon the disposition and subsequent inflation of the balloon in the hernial pocket.

Pursuant to another feature of the present invention, the balloon is provided with a one-way valve or other means for preventing deflation of the balloon prior to absorption thereof by body tissues into which the balloon has been inserted in a surgical operation.

A method for performing a hernia repair operation comprises, in accordance with the present invention, the steps of (a) inserting a balloon from an abdominal cavity of a patient through a hernial opening in an abdominal wall of the patient and into a hernial pocket in inguinal tissue, (b) inflating the balloon, and (c) sealing the abdominal opening. Because this method is performed from inside the abdominal cavity of the patient and because the balloon may be fastened in a collapsed configuration to the distal end of a rod or tube, the technique is readily performed in a laparoscopic operation. The balloon may be inserted into the abdominal cavity of the patient through a tubular port member in the abdominal wall.

Pursuant to another feature of the present invention, the step of sealing comprises the step of attaching to the abdominal wall of the patient, over the opening in the wall, a device for inducing human tissue growth. The device may take the form of a mesh web made of a biologically inert an flexible polymeric material.

Alternatively or additionally, a device for inducing human tissue growth may be inserted into the hernial pocket through the abdominal wall opening. The tissue growth inducement device in this case may take the form of a net-like member made of a biologically inert and flexible polymeric material. The net-like member preferably surrounds the balloon and is expanded from a collapsed configuration with the opening of the balloon.

Pursuant to another feature of the present invention, the surgical method further comprises the steps of (a) forming an aperture in a peritoneal lining of the patient prior to the step of inserting and (b) closing the aperture upon completion of the step of sealing.

According to an additional feature of the present invention, the balloon is attached to an elongate rod-like member. Then, the method includes the further step of severing the rod-like member proximate to the balloon upon the inflation of the balloon.

Preferably, as discussed hereinabove, the balloon is made of a material which is absorbable by the human body.

The present invention provides a quick and efficacious way of closing hernial openings.

The balloon is gradually dispersed or absorbed by the body, while the net and/or mesh web serves to close the tissues over the abdominal wall opening and the hernial pocket in the inguinal tissues.

Because the method and the associated instrument in accordance with the present invention are preferably used in a laparoscopic procedure, all the general advantages of that technique are in effect, including shortened hospital stay, reduced trauma to the patient, quicker operating time, and possibly reduced expense.

An instrument in accordance with the present invention is easy to use and is believed to be susceptible to efficient manufacturing techniques.

DETAILED DESCRIPTION

Figure 1:
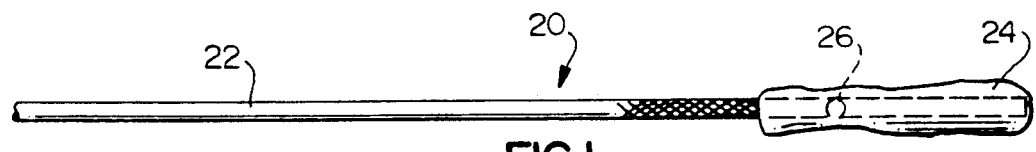
FIG. 1 is a side elevational view of a surgical instrument in accordance with the present invention, for use in a laparoscopic hernia repair operation, showing a balloon in a collapsed configuration.

As illustrated in FIG. 1, a surgical instrument 20 for use in laparoscopic hernia repair operations comprises an elongate hollow rod or tube 22 to a distal end of which a balloon 24 is attached. Prior to surgery, balloon 24 is disposed in a collapsed or deflated configuration about the distal end of tube 22. Tube 22 is provided with a one-way valve 26 through which air may be introduced under pressure into balloon 24. Balloon 24 is made of a material which is absorbable by or dispersible in the human body.

Figure 2:
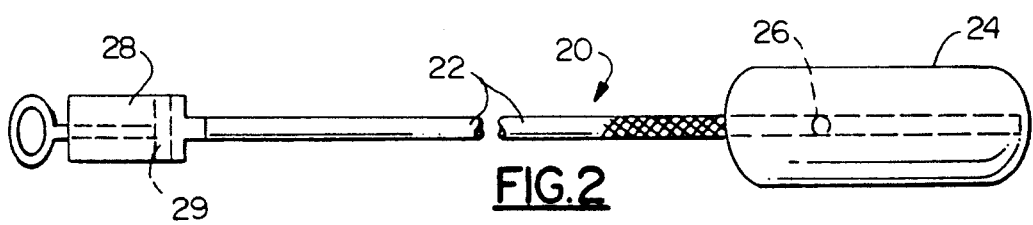
FIG. 2 is a side elevational view of the surgical instrument of FIG. 1, showing the balloon in an inflated configuration.

As shown in FIG. 2, a syringe or manual pump 28 or other controllable pressure source is securable to tube 22 at the proximal end thereof for forcing air through tube 22 and one-way valve 26 into balloon 24. FIG. 2 shows balloon 24 in an expanded configuration into which the balloon is inflated subsequently to the insertion of the balloon into an inguinal canal or hernial pocket during a hernia repair operation.

Figure 3:
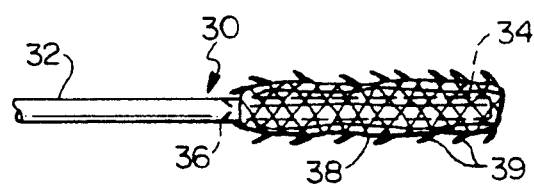
FIG. 3 is a partial side elevational view of another surgical instrument in accordance with the present invention, showing a balloon with an enveloping net, both in a collapsed or deflated configuration.
Figure 4:
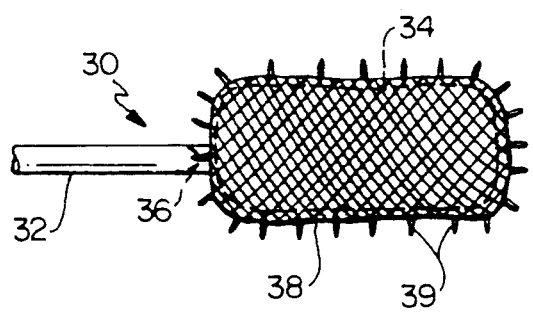
FIG. 4 is a partial side elevational view of the surgical instrument of FIG. 3, showing the balloon and net of that drawing figure in an inflated or expanded configuration.

FIGS. 3 and 4 illustrate another surgical instrument 30 usable to close a hernial opening during a laparoscopic procedure. Surgical instrument 30 comprises a hollow rod or tubular member 32 to a distal end of which a balloon 34 is attached. Balloon 34 is made of a material which is absorbable by or dispersible in the human body. Prior to surgery, balloon 34 is disposed in a collapsed or deflated configuration about the distal end of tubular member 32. Tubular member 32 is provided with a one-way valve 36 through which air may be introduced under pressure into balloon 34.

As discussed hereinabove with respect to FIG. 2, a syringe or manual pump 28 or other controllable pressure source is securable to tubular member 32 at the proximal end thereof for forcing air through tubular member 32 and one-way valve 36 into balloon 34. FIG. 4 shows balloon 34 in an expanded configuration into which the balloon is inflated subsequently to the insertion of the balloon into an inguinal canal or hernial pocket during a hernia repair operation.

As further illustrated in FIGS. 3 and 4, surgical instrument 30 includes a flexible net or mesh envelope 38 which surrounds balloon 34 and which is made of a biologically inert polymeric material such as polyethylene. Prior to the commencement of a laparoscopic hernia repair operation, net or mesh envelope 38 is disposed in a collapsed configuration together with balloon 34 at the distal end of tubular member 32. Upon the inflation of balloon 34, as described in detail hereinafter with reference to FIGS. 8A-8R, net or envelope 38 also expands, as illustrated in FIG. 4. Net or envelope 38 is provided with a multiplicity of projections or fingers 39 which extend outwardly from the net in the expanded configuration thereof, as seen in FIG. 4. In the collapsed configuration of net 38, projections 39 may be folded or otherwise retracted, owing to the flexible collapse of net 38. Projections 39 serve to fix net 38 to the tissues of the inguinal canal, thereby anchoring net 38 and balloon 34 in place upon the completion of a laparoscopic hernia repair operation.

Figure 5:
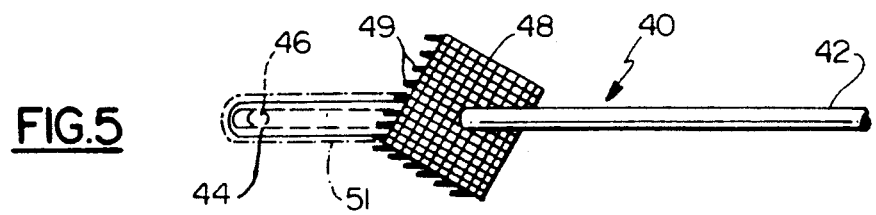
FIG. 5 is a partial perspective view of yet another surgical instrument in accordance with the present invention, showing a balloon in a collapsed configuration and a mesh web.
Figure 6:
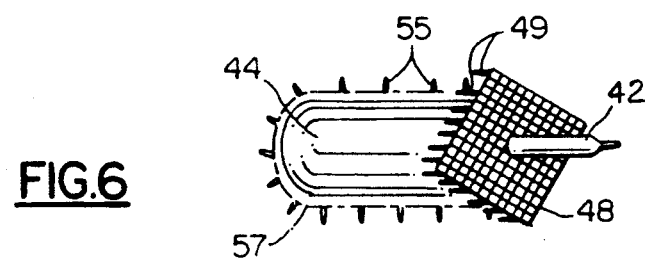
FIG. 6 is a partial perspective view of the surgical instrument of FIG. 5, showing the balloon in an inflated configuration.
Figure 7:
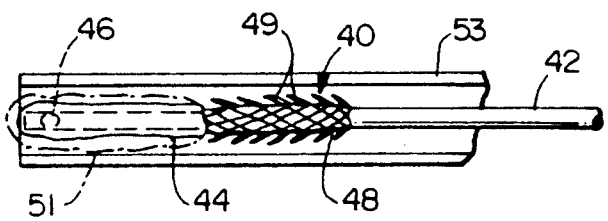
FIG. 7 is a partial side elevational view of the surgical instrument of FIGS. 5 and 6, showing the balloon and the mesh web in a folded or collapsed configuration inside an insertion tube.

As illustrated in FIGS. 5-7, another surgical instrument 40 for use in a laparoscopic hernia repair operation comprises a hollow rod or tubular member 42 carrying at a distal end an inflatable balloon 44 made of a material which is absorbable by or dispersible in the human body. Balloon 44 exists in a collapsed or deflated configuration prior to a hernia repair operation. Tubular member 42 is provided with a one-way valve 46 through which air may be introduced under pressure into balloon 44. A mesh web 48 is also attached to tubular member 42 the proximal end of balloon 44. Mesh web 48 is provided on a distal side with a multiplicity of distally extending projections or fingers 49. Projections 49 serve to fix mesh 48 to the tissues of the abdominal wall, thereby anchoring mesh 48 and balloon 44 in place upon the completion of a laparoscopic hernia repair operation.

As indicated by dot-dash lines in FIGS. 5-7, surgical instrument 40 may further comprise a flexible net or mesh envelope 51 which surrounds balloon 44 and which is made of a biologically inert polymeric material such as polyethylene. Prior to the commencement of a laparoscopic hernia repair operation, net or mesh envelope 51 is disposed in a collapsed configuration together with balloon 44 at the distal end of tubular member 42 inside an outer tubular insertion member 53. Tubular insertion member 53 is preferably used with each surgical instrument 20, 30, and 40 to insert the distal end of tubular members 22, 32, and 42 into a patient during a laparoscopic hernia repair operation.

Upon an inflation of balloon 44, as described in detail hereinafter with reference to FIGS. 8A-8R, net or envelope 51 also expands, as illustrated in FIG. 6. Net or envelope 51 is provided with a multiplicity of projections or fingers 55 which extend outwardly from the net in the expanded configuration thereof, as seen in FIG. 6. In the collapsed configuration of net 51, projections 55 may be folded back upon the body of net 51 or otherwise retracted, owing to the flexible nature of net 51. In the extended use configuration of FIG. 6, projections 55 serve to fix net 51 to the tissues of the inguinal canal, thereby providing an additional anchoring function supplementing the attachment action of projections 49 of mesh 48.

FIG. 6 shows tubular member 42 as a stub which remains after the tubular member has been crimped and severed during a laparoscopic hernia repair operation, as described hereinafter with reference particularly to FIGS. 8J and 8K.

Figure 8A:
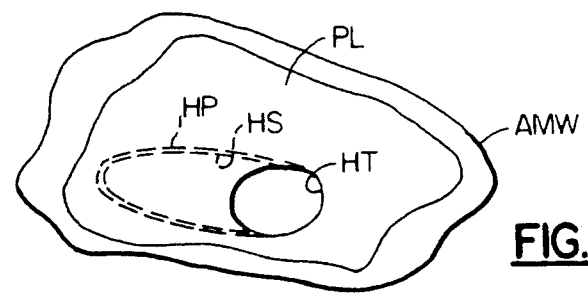
FIGS. 8A-8R are diagrammatic partial perspective views showing successive steps in a hernia repair operation in accordance with the present invention.

FIG. 8A depicts a hernial opening or tear HT in an abdominal muscle wall AMW of a patient and a hernial pocket HP in the adjacent inguinal ring or inguinal tissue. A portion of the peritoneum or peritoneal lining PL has slipped through hernial opening HT and forms a hernial sac HS inside the inguinal tissue.

Figure 8B:
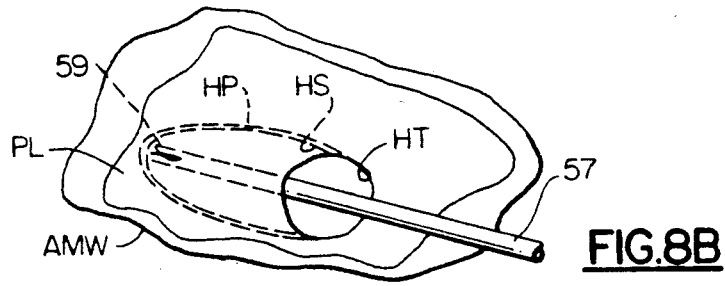

FIG. 8B illustrates a distal end portion of a laparoscopic clamp 57 passed through hernial opening HT into hernial sac HS. A surgeon viewing the surgical site through a laparoscope (not illustrated) manipulates laparoscopic clamp 57 from outside the patient to actuate clamping forceps 59 at the distal tip of laparoscopic clamp 57 to grip hernial sac HS.

Figure 8C:
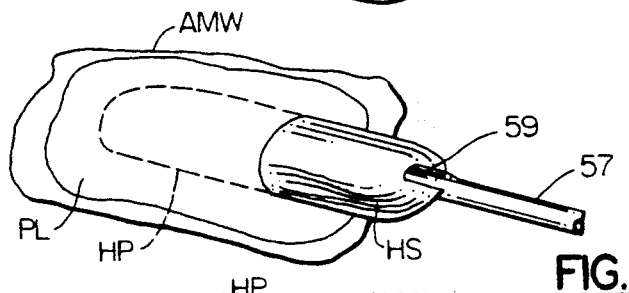
Figure 8D:
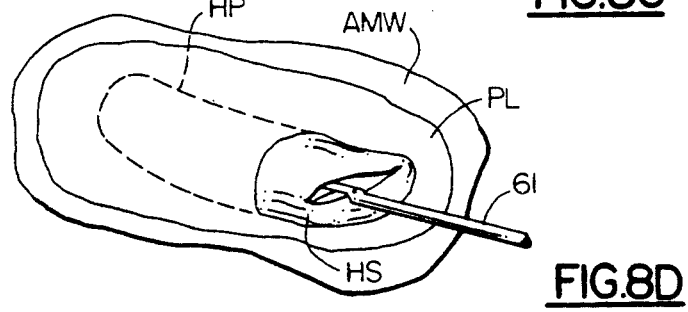
Figure 8E:
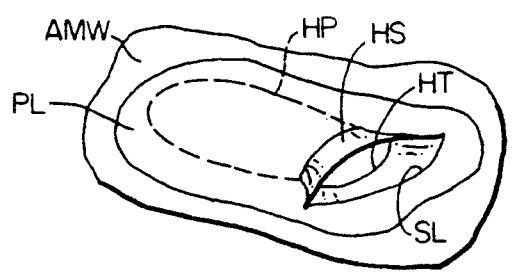
Figure 8F:
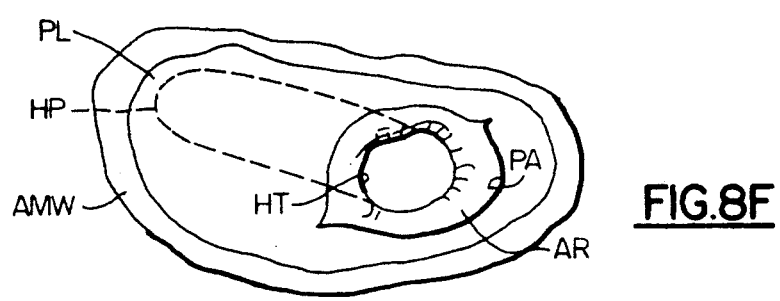

Upon the clamping of hernial sac HS, the operating surgeon pulls laparoscopic clamp 57 so that hernial sac HS is inverted through hernial opening HT, as illustrated in FIG. 8C. As shown in FIG. 8D, laparoscopic scissors 61 are then used to cut hernial sac HS. FIG. 8E illustrates an intermediate stage in the cutting of hernial sac HS: a portion of abdominal muscle wall AMW is visible through a slit SL formed in peritoneal lining PL. Upon the completion of the cutting procedure, an aperture PA is formed in peritoneal lining PL so that a ring shaped surface AR of abdominal muscle wall AMW is visible through aperture PA.

Figure 8G:
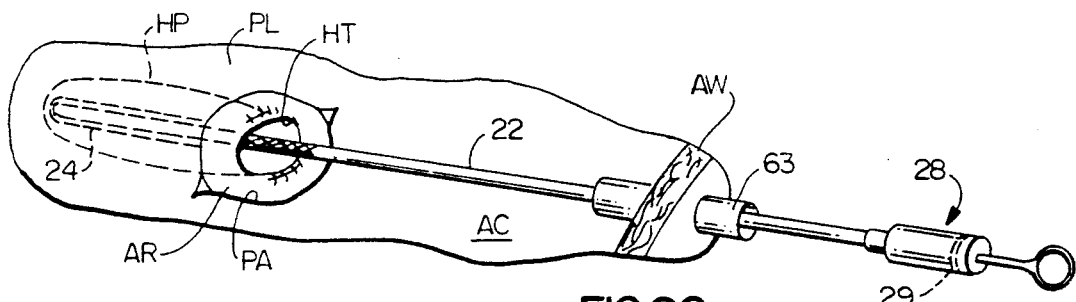

As illustrated in FIG. 8G, tubular member 22 of surgical instrument 20 is passed through a tubular port member 63 which traverses an abdominal wall portion AW of the patient. Pursuant to conventional laparoscopic surgical procedures, a trocar (not shown) is used to pierce abdominal wall AW. Port member 63 remains in the opening which is formed by the trocar. The abdominal wall AW is then lifted, for example, by conventional abdomen pressurization techniques. As further illustrated in FIG. 8G, the distal end of tubular member 22 of surgical instrument 20 is passed through hernial opening HT into hernial pocket HP so that balloon 24 is located essentially completely within the hernial pocket.

Figure 8H:
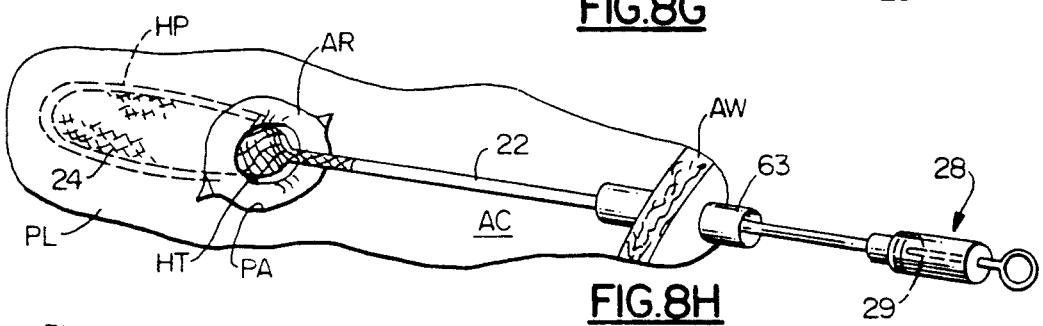

Upon the successful disposition of balloon 24 inside hernial pocket HP, hypodermic syringe 28 is actuated to inflate the balloon. FIGS. 8G and 8H show hypodermic syringe 28 before and after a pressurization stroke of a plunger component 29 of the syringe. In a subsequent step depicted in FIG. 8I, a laparoscopic clamp 65 is passed into the abdominal cavity AC of the patient and is manipulated from outside the patient to crimp or crush a portion of tubular member 22 immediately proximal of balloon 24. Laparoscopic clamp 65 is inserted into the abdominal cavity of the patient through another tubular port member (not shown) introduced into abdominal wall AW via, for example, the conventional trocar piercing technique.

Figure 8I:
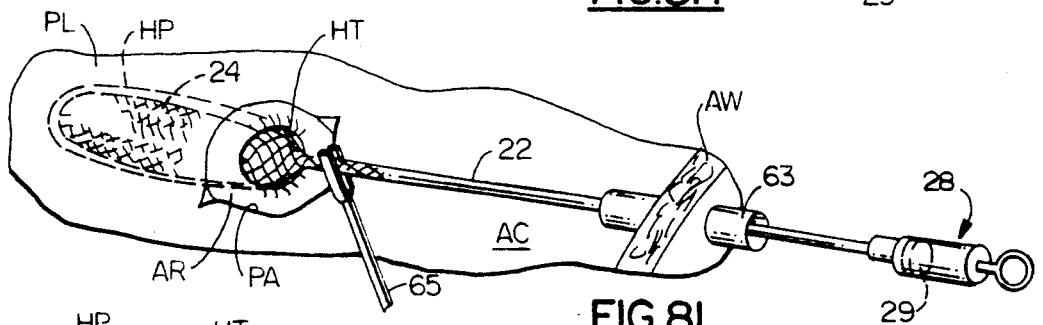
Figure 8J:
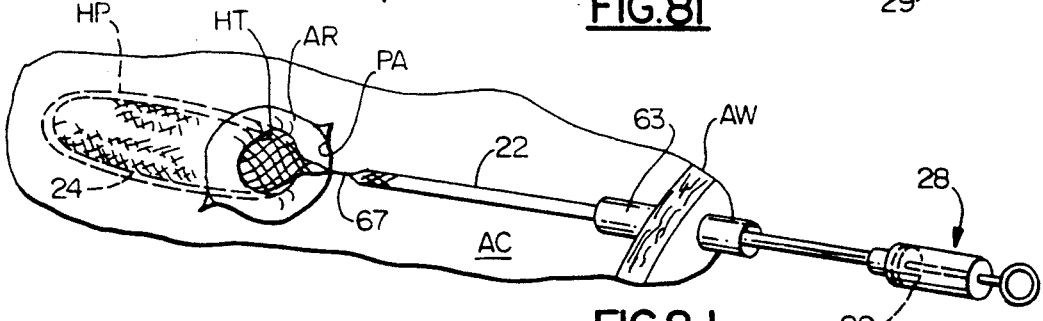

FIG. 8J shows tubular member 22 with a crushed or crimped section 67 after the removal of laparoscopic clamp 65. A laparoscopic scissors 69 is then inserted into abdominal cavity AC through the second tubular port member (not shown) and actuated to sever tubular member 22 at crimped section 67. Upon the severing of tubular member 22 at crimped section 67, the severed proximal portion of tubular member 22 is removed via tubular port member 63 (FIG. 8L), leaving a stub of tubular member 22 attached to inflated balloon 24.

Figure 8K:
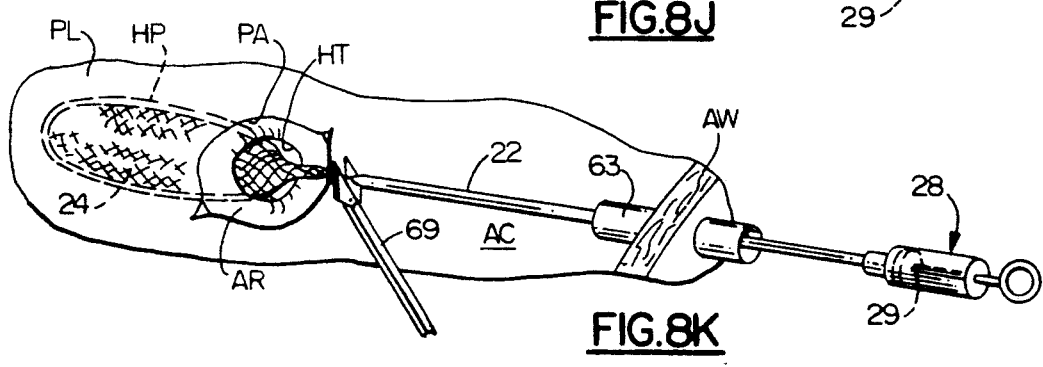
Figure 8L:
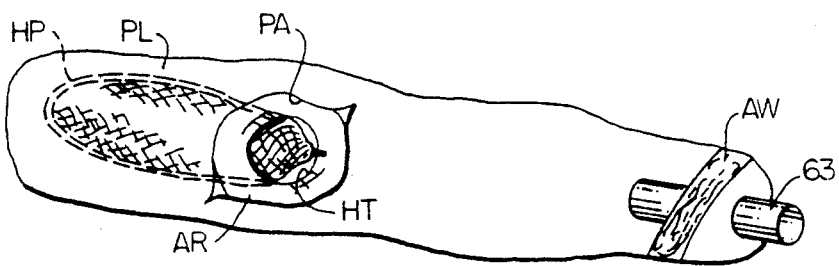

It is to be noted that the crimping and severing steps of FIGS. 8I and 8K are intended to seal tubular member 22 and close balloon 24 particularly in the event that no one-way valve is provided in surgical instrument 20. Where the surgical hernia repair instrument includes an efficacious one-way valve, e.g. valve 26 (FIG. 1 and 2), then the crimping and severing steps of FIGS. 8I and 8K may be implemented by the same surgical instrument, e.g., a laparoscopic cutting forceps. In the latter case, the closure of tubular member 22 is not especially critical. It is to be further noted that tubular member 22 may be internally provided in the area of crimped section 67 with an adhesive coating (not illustrated) or other means for effectuating an airtight sealing of the tubular member.

Figure 8M:
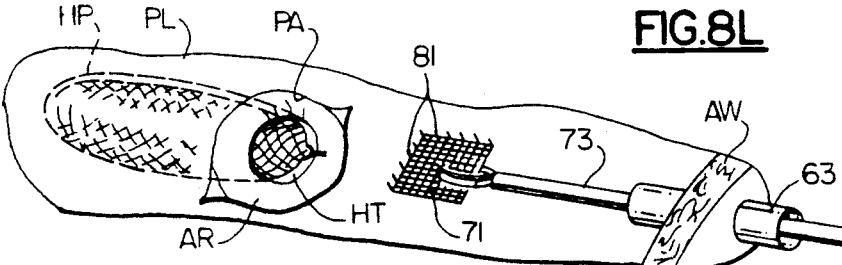
Figure 8N:
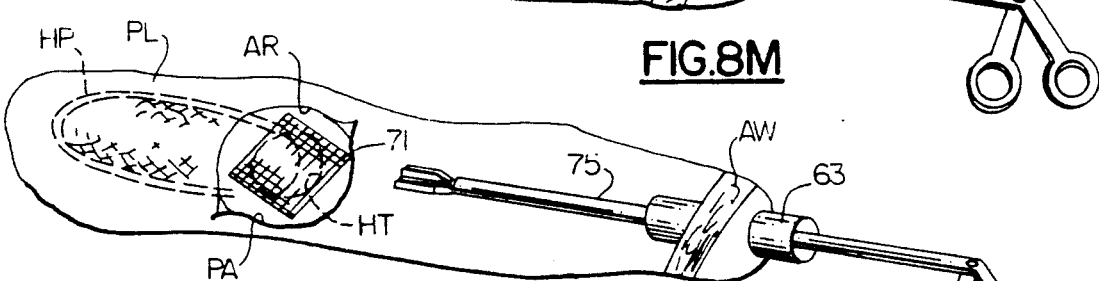

Balloon 24 is locked into position within hernial pocket HP via the attachment of a mesh patch 71 to abdominal muscle wall AMW to cover hernial opening HT, as illustrated in FIGS. 8M, 8N, 8P, and 8Q. Mesh patch 71 is made of a biologically inert polymeric material such as polyethylene and is introduced into abdominal cavity AC by a clamping forceps 73 which is passed through port member 63 (FIG. 8M). Mesh patch 71 is placed on abdominal muscle wall AMW, specifically on ring shaped surface AR thereof, so as to close hernial opening HT and cover balloon 24.

Figure 8P:
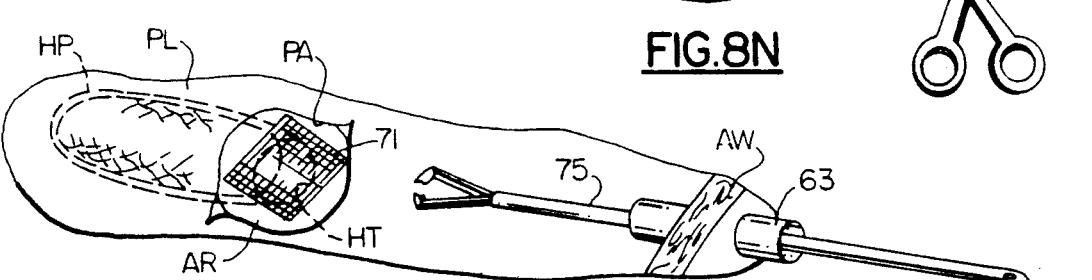

Upon the successful disposition of mesh patch 71 (FIG. 8N), clamping forceps 73 is removed via port member 63 and a laparoscopic stapling device 75 is then inserted through the port member, as depicted in FIG. 8P. Laparoscopic stapling device 75 is used to apply a plurality of staples 77 through mesh patch 71 and abdominal muscle wall AMW in the area of ring shaped surface AR, thereby attaching the mesh patch to the abdominal muscle wall AMW to permanently close hernial opening HT and secure balloon 24 in hernial pocket HP.

Figure 8Q:
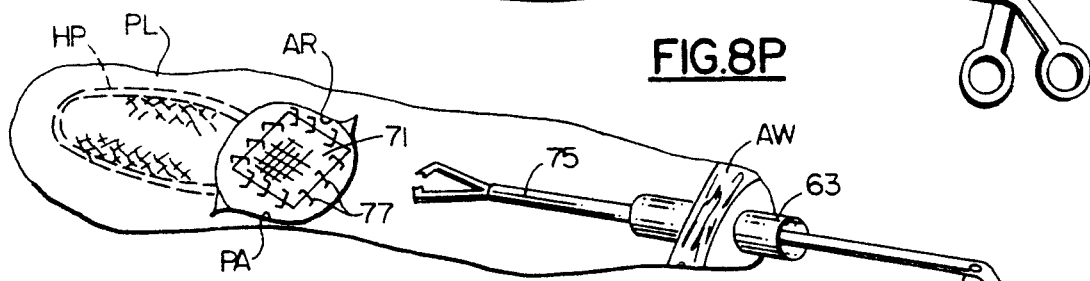
Figure 8R:
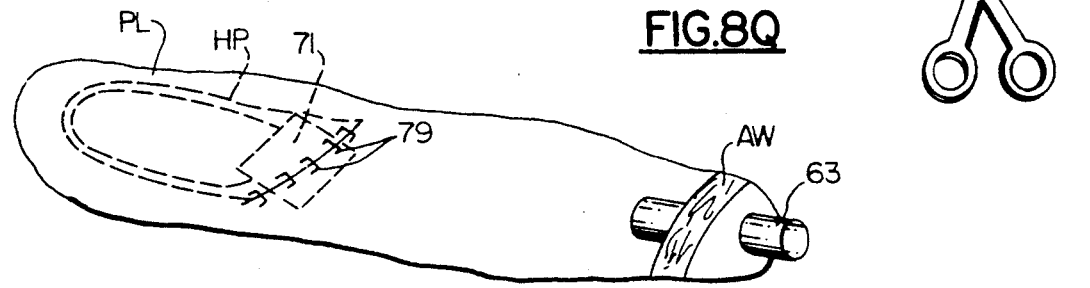

As shown in FIG. 8R, laparoscopic stapling device 75 is then used to apply another series of staples 79 to peritoneal lining PL to close peritoneal aperture PA over mesh patch 71.

As illustrated in FIG. 8M, mesh patch 71 may include a plurality of pin-like projections 81 which extend into abdominal muscle wall AMW upon the disposition of mesh patch 71 over hernial pocket HP. The projections serve to temporarily fix mesh patch 71 to abdominal muscle wall AMW, prior to the laparoscopic stapling of mesh patch 71 to abdominal muscle wall AMW.

Mesh patch 71 serves to induce or accelerate the growth of abdominal tissue over hernial opening HT, to naturally close hernial pocket HP. As discussed hereinabove with reference to FIGS. 3 and 4, surgical hernial repair instrument 30 includes net 38 for accelerating the growth of inguinal tissue about hernial pocket HP. Surgical instrument 30 is applied in the same sequence of steps as discussed with reference to FIGS. 8A-8R. The use of surgical instrument 40 simplifies the procedure of FIGS. 8A-8R insofar as mesh web 48 is applied automatically to abdominal muscle wall AMW during the disposition of balloon 44 within hernial pocket HP.

A stapling device which may be used in the laparoscopic stapling steps of FIGS. 8P, 8Q, and 8R is disclosed in U.S. Pat. No. 5,015,249, the disclosure of which is hereby incorporated by reference.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A surgical instrument for use in repairing an internal body organ of a patient, comprising:
    an elongate rod-like member having a distal end and a proximal end;
    a balloon detachably attached in a collapsed configuration to said rod-like member at said distal end, said balloon being expandable from the collapsed configuration to an expanded configuration, said balloon being made of a material which is absorbable by the human body; and
    inflation means operatively connected to said balloon for enabling an expansion of said balloon from said collapsed configuration to said expanded configuration.

2. The instrument defined in claim 1, further comprising means attached to said balloon for inducing human tissue growth upon insertion and inflation of said balloon in a hernial pocket of a patient and upon subsequent absorption of said balloon by internal tissues of the patient.

3. The instrument defined in claim 2 wherein said means for inducing includes a net-like member attached in a collapsed configuration to said rod-like member at said distal end, said net-like member enveloping said balloon, said net-like member being made of a biologically inert and flexible polymeric material.

4. The instrument defined in claim 3 wherein said net-like member is formed with a plurality of outwardly extending projections.

5. The instrument defined in claim 2 wherein said means for inducing includes a mesh web attached to said balloon at a proximal end thereof.

6. The instrument defined in claim 5 wherein said mesh web is formed with a plurality of outwardly extending projections.

7. The instrument defined in claim 2 wherein at least a portion of said tube proximate to said balloon and located proximally thereof is deformable.

8. The instrument defined in claim 1 wherein said rod-like member is hollow and thereby takes the form of a tube.

9. The instrument defined in claim 1, further comprising means operatively attached to said balloon for preventing deflation thereof prior to absorption of the material of said balloon by body tissues into which said balloon has been inserted in a surgical operation.

10. The instrument defined in claim 9 wherein said means for preventing includes a one-way valve.

11. A method for performing a hernia repair operation, comprising the steps of:
    forming an aperture in a peritoneal lining of a patient;
    upon completion of said step of forming, inserting a balloon from an abdominal cavity of the patient through said aperture and a hernial opening in an abdominal wall of the patient and into a hernial pocket in inguinal tissue;
    inflating said balloon;
    sealing said opening; and
    closing said aperture upon completion of said step of sealing.

12. The method defined in claim 11 wherein said step of sealing comprises the step of attaching to the abdominal wall of the patient over said opening means for inducing human tissue growth.

13. The method defined in claim 12 wherein said means for inducing human tissue growth takes the form of a mesh web made of a biologically inert and flexible polymeric material.

14. The method defined in claim 11, further comprising the step, performed prior to said step of sealing, of inserting into said hernial pocket through said opening means for inducing human tissue growth.

15. The method defined in claim 14 wherein said means for inducing human tissue growth takes the form of a net-like member made of a biologically inert and flexible polymeric material, further comprising the step of opening said net-like member from a collapsed configuration.

16. The method defined in claim 15 wherein said net-like member surrounds said balloon, said step of opening comprising the step of expanding said net-like member by inflating said balloon.

17. The method defined in claim 11 wherein said balloon is attached to an elongate rod-like member, further comprising the step of severing said rod-like member proximate to said balloon upon completion of said step of inflating.

18. The method defined in claim 11 wherein said balloon is made of a material which is absorbable by the human body.

19. A surgical instrument for use in repairing an internal body organ of a patient, comprising:
    an elongate rod-like member having a distal end and a proximal end;
    a balloon detachably attached in a collapsed configuration to said rod-like member at said distal end, said balloon being expandable from the collapsed configuration to an expanded configuration, said balloon being made of a material which is absorbable by the human body;
    inflation means operatively connected to said balloon for enabling an expansion of said balloon from said collapsed configuration to said expanded configuration; and
    unitary means made of a biologically inert and flexible polymeric material attached to said balloon and substantially enveloping same for inducing human tissue growth upon insertion and inflation of said balloon in a hernial pocket of a patient and upon subsequent absorption of said balloon by internal tissues of the patient.

20. The instrument defined in claim 19 wherein said means for inducing includes a net-like member attached in a collapsed configuration to said rod-like member at said distal end.

21. A surgical instrument for use in repairing an internal body organ of a patient, comprising:
    an elongate rod-like member having a distal end and a proximal end;
    a balloon detachably attached in a collapsed configuration to said rod-like member at said distal end, said balloon being expandable from the collapsed configuration to an expanded configuration, said balloon being made of a material which is absorbable by the human body;

inflation means operatively connected to said balloon for enabling an expansion of said balloon from said collapsed configuration to said expanded configuration; and means attached to said balloon for inducing human tissue growth upon insertion and inflation of said balloon in a hernial pocket of a patient and upon subsequent absorption of said balloon by internal tissues of the patient, said means for inducing including a substantially planar mesh web attached to said balloon at a proximal end thereof.

22. A method for performing a hernia repair operation, comprising the steps of:

inserting a balloon from an abdominal cavity of a patient through a hernial opening in an abdominal wall of the patient and into a hernial pocket in inguinal tissue, said balloon being attached to an elongate rod-like member;

inflating said balloon;

severing said rod-like member proximate to said balloon upon completion of said step of inflating; and sealing said opening.

* * * * *